United States Patent [19]
Arakawa

[11] Patent Number: 5,665,976
[45] Date of Patent: Sep. 9, 1997

[54] RADIATION IMAGE READ-OUT AND ERASING METHOD AND APPARATUS

[75] Inventor: Satoshi Arakawa, Kanagawa-ken, Japan

[73] Assignee: Fuji Photo Film Co., Ltd., Kanagawa, Japan

[21] Appl. No.: 708,692

[22] Filed: Sep. 5, 1996

[30] Foreign Application Priority Data

Sep. 5, 1995 [JP] Japan ................. 7-28185

[51] Int. Cl.$^6$ ................................ G01N 23/04
[52] U.S. Cl. ................................ 250/588
[58] Field of Search ........................ 250/588

[56] References Cited

U.S. PATENT DOCUMENTS

| 5,065,021 | 11/1991 | Arakawa | 250/588 |
| 5,237,177 | 8/1993 | Kimura | 250/580 |
| 5,550,386 | 8/1996 | Kojima et al. | 250/588 |

FOREIGN PATENT DOCUMENTS

| 63-298333 | 12/1988 | Japan . |
| 3256038 | 11/1991 | Japan . |

*Primary Examiner*—Carolyn E. Fields
*Attorney, Agent, or Firm*—Sughrue, Mion, Zinn, Macpeak & Seas

[57] ABSTRACT

A radiation image stored on a stimulable phosphor sheet is read-out by exposing the stimulable phosphor sheet to stimulating rays, photoelectrically detecting light emitted by the stimulable phosphor sheet by a photomultiplier and converting it into an electric image signal in a read-out section while feeding the stimulable phosphor sheet through a read-out section toward an erasing section. Residual radiation image information on the stimulable phosphor sheet is erased by exposing the portion of the stimulable phosphor sheet which is fed to the erasing section after passing through the read-out section to first erasing light, and exposing the stimulable phosphor sheet to second erasing light while feeding the stimulable phosphor sheet through the erasing section toward the read-out section. The first erasing light contains no light component in a wavelength range which can be detected by the photomultiplier and the second erasing light contains a light component in the wavelength range which can be detected by the photomultiplier read-out means.

6 Claims, 2 Drawing Sheets

RADIATION IMAGE READ-OUT AND ERASING METHOD AND APPARATUS

BACKGROUND OF THE INVENTION

1. Field of the Invention

This invention relates to a radiation image read-out and erasing method for reading out a radiation image stored on a stimulable phosphor sheet and erasing the residual image information remaining on the stimulable phosphor sheet and to an apparatus for carrying out the method.

2. Description of the Related Art

When certain kinds of phosphors are exposed to radiation such as X-rays, α-rays, β-rays, γ-rays, cathode rays or ultraviolet rays, they store a part of the energy of the radiation. Then, when the phosphor which has been exposed to the radiation is exposed to stimulating rays such as visible light, light is emitted from the phosphor in proportion to the stored energy of the radiation. A phosphor exhibiting such properties is referred to as "a stimulable phosphor".

It has been proposed to use stimulable phosphors in radiation image recording and reproducing systems. Specifically, a radiation image of an object, such as a human body, is recorded on a recording medium provided with a layer of the stimulable phosphor. Though the recording medium may be in various forms such as a sheet, a panel, a drum and the like, it will be referred to as "a stimulable phosphor sheet", hereinbelow. The stimulable phosphor sheet, on which the radiation image has been stored, is then exposed to stimulating rays, such as a laser beam, which cause it to emit light in proportion to the amount of energy stored thereon during its exposure to the radiation. The light emitted by the stimulable phosphor sheet, upon stimulation thereof, is photoelectrically detected and converted into an electric image signal. The image signal is then processed and used for the reproduction of the radiation image of the object as a visible image suitable for diagnosis. See Japanese Unexamined Patent Publication No. 56(1981)-11395 and U.S. Pat. Nos. 4,258,264, 4,315,318, 4,387,428, and 4,276,473.

In such a system, it is said that it is preferred to use light rays within the wavelength range of 600 to 700 nm as the stimulating rays and to detect light emitted by the stimulable phosphor sheet upon stimulation thereof within the wavelength range of 300 to 500 nm in order to separate the stimulating rays from the light emitted by the stimulable phosphor sheet upon stimulation thereof so that even feeble emission can be effectively detected. It is further said that stimulable phosphors which emit light within the wavelength range of 300 to 500 nm upon stimulation by stimulating rays within the wavelength range of 600 to 700 nm are preferably used. (See U.S. Pat. No. 4,258,264.)

From the economical viewpoint, it is preferred that the stimulable phosphor sheet be repeatedly used.

Though the radiation energy stored on the stimulable phosphor sheet during exposure to radiation passing through an object should be released from the stimulable phosphor sheet when the intensity of the stimulating light rays to which the stimulable phosphor sheet is exposed during read-out of the radiation image is sufficient, actually the radiation energy stored on the stimulable phosphor sheet cannot be completely released by only the stimulating light rays, and a part of the radiation energy is kept on the stimulable phosphor sheet as residual radiation energy. The residual radiation energy can appear as noise in a radiation image taken next when the stimulable phosphor sheet is reused.

Further since a fine amount of radioelements such as $^{226}$Ra, $^{40}$K and the like are contained in the stimulable phosphors, the stimulable phosphor sheet stores thereon radiation energy of radiation from the radioelements even if it is left to stand, and the radiation energy thus stored can cause noise. Further energy of environmental radiations such as cosmic radiations, radiations from radioactive isotopes in the environment and the like can be stored on the stimulable phosphor sheet. Such radiation energy stored on the stimulable phosphor sheet while the stimulable phosphor sheet is left to stand appears as fogging in a radiation image taken next. This applicant has proposed a method of causing a stimulable phosphor sheet to sufficiently release radiation energy stored thereon in order to prevent fogging due to radiation energy stored while the stimulable phosphor sheet is left to stand and noise due to residual radiation energy from appearing in a radiation image subsequently taken by exposing the stimulable phosphor sheet to erasing light containing therein light component having a wavelength within the stimulating wavelength range of the stimulable phosphors before recording a radiation image on the stimulable phosphor sheet.

As such erasing methods, there have been known those in which a light source emitting light of a relatively long wavelength such as a tungsten lamp which emits visible light or infrared radiation, a halogen lamp or an infrared lamp is employed as the erasing light source (U.S. Pat. No. 4,400,619), in which a light source emitting light of a relatively short wavelength (about 400 to 600 nm) such as a fluorescent tube, a laser, a Na lamp, a Ne lamp, a metal halide lamp or a Xe lamp is employed as the erasing light source (U.S. Pat. No. 4,496,838), and in which the stimulable phosphor sheet is exposed to erasing light twice, the second erasing being carried out just before the stimulable phosphor sheet is reused by exposing the stimulable phosphor sheet to erasing light which is 1/5 to 3/10000 of that used in the first erasing in amount (U.S. Pat. No. 4,439,682). It is said that erasure can be most efficiently effected when visible light is employed as the erasing light.

However when the erasing light contains no wavelength in the ultraviolet region, residual radiation energy carried by trapped electrons at a relatively deep level which is hard to release by visible light cannot be sufficiently erased. On the other hand, when the erasing light contains a large amount of wavelengths in the ultraviolet region, new trapped electrons are formed by the erasing light in the ultraviolet region though the residual radiation energy carried by trapped electrons at a relatively deep level can be erased.

Thus it has been very difficult to efficiently erase radiation energy carried by both the normal trapped electrons and trapped electrons at a relatively deep level, and accordingly, for instance, when a high-sensitive radiation image recording is carried out, the residual radiation energy affects the quality of the image. At present, in order to overcome such a problem, the short wavelength component of the erasing light has to be finely controlled. Thus there has been proposed a method of erasing residual radiation energy in which the stimulable phosphor sheet is first erased by erasing light containing a wavelength component in the ultraviolet region and then erased by erasing light having a wavelength longer than the ultraviolet region so that radiation energy carried by trapped electrons at a deep level can be erased as well as radiation energy carried by trapped electrons at normal level. (U.S. Pat. No. 5,065,021)

There also has been proposed a simultaneous read-out and erasing apparatus in which a read-out section having a photoelectric read-out means for reading out a radiation image on the stimulable phosphor sheet is disposed adjacent to an erasing section for erasing residual radiation energy on the stimulable phosphor sheet and while the radiation image on the stimulable phosphor sheet is being read out from one end to the other end of the stimulable phosphor sheet, erasing light is projected onto the stimulable phosphor sheet from said one end to the other following the read-out operation. See, for instance, Japanese Unexamined Patent Publication No. 4(1992)-32046. With this apparatus, read-out and erasure can be efficiently carried out in a short time.

However an attempt to employ the erasing method disclosed in U.S. Pat. No. 5,065,021 in carrying out simultaneous read-out and erasing will encounter the following difficulties. That is, when erasing light in the ultraviolet region is employed in the erasing operation following the read-out operation, the erasing light can be detected by the photoelectric read-out means to generate noise in a reproduced radiation image since the wavelength range of the light emitted from the stimulable phosphor sheet upon stimulation thereof is relatively close to the ultraviolet region.

Generally the photoelectric read-out means is provided with a stimulating ray cut filter which cuts the stimulating rays and accordingly when light of a wavelength to be cut by the stimulating ray cut filter is employed as the erasing light, the erasing light cannot generate noise in a reproduced radiation image.

However when the light of a wavelength to be cut by the stimulating ray cut filter is employed as the erasing light, erasing efficiency is low and the residual radiation energy cannot be sufficiently erased.

Thus in the simultaneous read-out and erasing system, the residual radiation energy cannot be sufficiently erased and noise is generated in a reproduced radiation image, which results in deterioration in quality of the reproduced radiation image.

SUMMARY OF THE INVENTION

In view of the foregoing observations and description, the primary object of the present invention is to provide a radiation image read-out and erasing method which can better erase the residual radiation energy on a stimulable phosphor sheet without generating noise in a reproduced radiation image in a simultaneous read-out and erasing.

Another object of the present invention is to provide an apparatus for carrying out the method.

In accordance with the present invention, while feeding a stimulable phosphor sheet through a read-out section toward an erasing section, the stimulable phosphor sheet is exposed to stimulating rays in the read-out section to read out a radiation image stored thereon and the portion of the stimulable phosphor sheet which is fed to the erasing section after passing through the read-out section is subjected to a first erasure where the stimulable phosphor sheet is exposed to first erasing light. Then while feeding the stimulable phosphor sheet through the erasing section toward the read-out section, the stimulable phosphor sheet is subjected to a second erasure where the stimulable phosphor sheet is exposed to second erasing light. The first erasing light contains no light component in a wavelength range which can be detected by the photoelectric read-out means and the second erasing light contains a light component in the wavelength range which can be detected by the photoelectric read-out means.

It is preferred that after the second erasure, the stimulable phosphor sheet be further exposed to erasing light which contains no light component having a wavelength shorter than the light emitted from the stimulable phosphor sheet upon stimulation thereof.

Further it is preferred that the first erasing light has a wavelength longer than that of the light emitted from the stimulable phosphor sheet upon stimulation thereof, and the second erasing light contains a light component having a wavelength not longer than that of the light emitted from the stimulable phosphor sheet upon stimulation thereof.

The first erasure is carried out concurrently with the read-out of the radiation image with the photoelectric read out means operated. In the first erasure, the first erasing light which contains no light component in a wavelength range which can be detected by the photoelectric read-out means is employed and accordingly the first erasing light is not received by the photoelectric read-out means to generate noise in a reproduced radiation image. The second erasure is carried out after completion of the read-out operation with the photoelectric read-out means stopped. Accordingly the second erasing light cannot be received by the photoelectric read-out means to generate noise in a reproduced radiation image and therefore the second erasing light may contain light components having a wavelength within the ultraviolet region which is relatively close to the wavelength range of the light emitted from the stimulable phosphor sheet upon stimulation thereof and can be detected by the photoelectric read-out means, whereby electrons trapped deep in the stimulable phosphor sheet can be released. Thus in accordance with the present invention, the residual radiation energy on the stimulable phosphor sheet can be sufficiently erased without generation of noise by the erasing light, whereby a high quality image can be reproduced.

Further when after the second erasure, the stimulable phosphor sheet is further exposed to third erasing light which contains no light component having a wavelength shorter than the light emitted from the stimulable phosphor sheet upon stimulation thereof, components excited by the second erasing light can be erased, if any.

DESCRIPTION OF THE PREFERRED EMBODIMENTS

Figure 1:
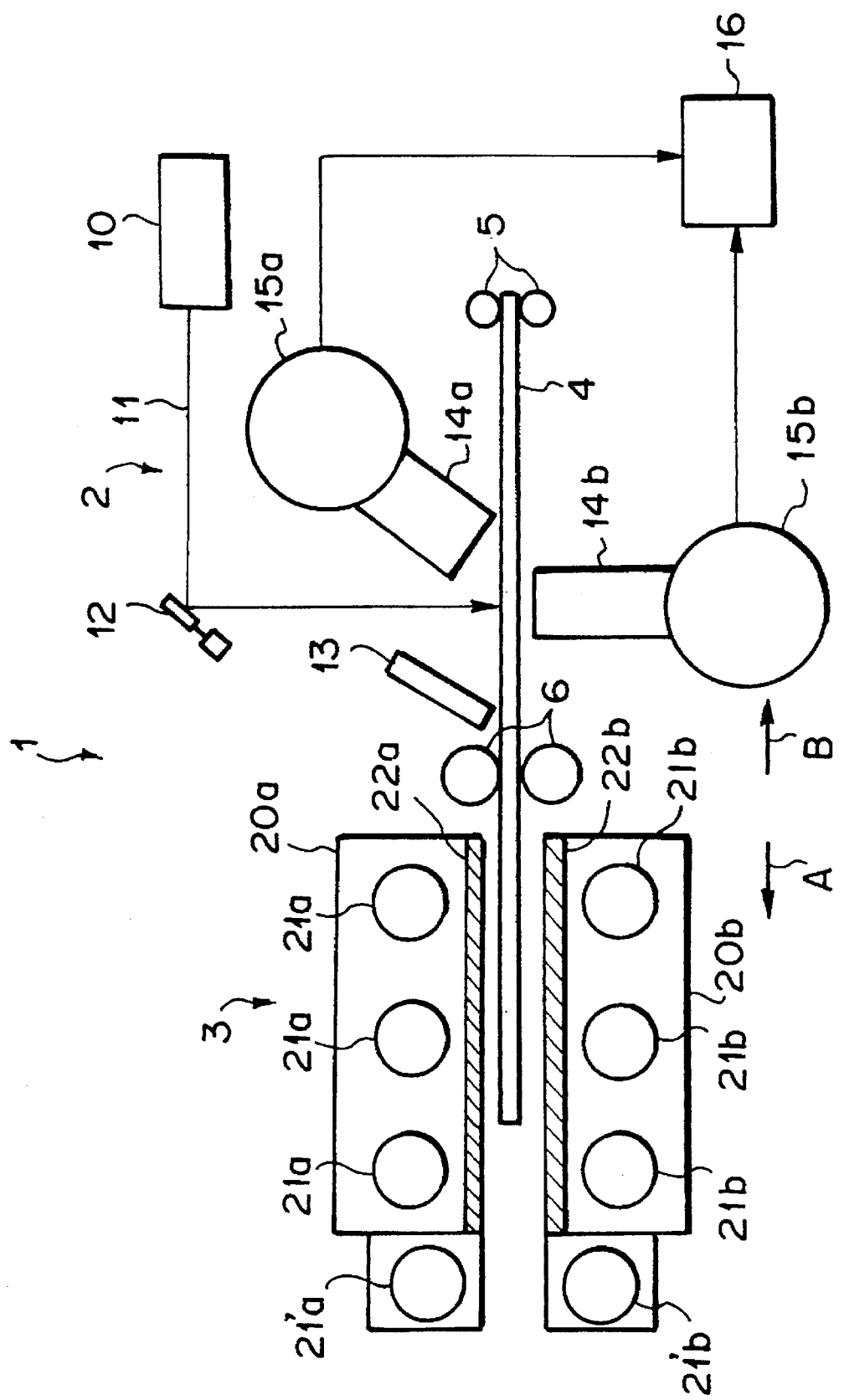
FIG. 1 is a schematic view of a radiation image read-out and erasing apparatus in accordance with an embodiment of the present invention.

As shown in FIG. 1, a radiation image read-out and erasing apparatus i in accordance with an embodiment of the present invention comprises a read-out section 2 for reading out a radiation image stored on a stimulable phosphor sheet 4 and an erasing section 3 for erasing residual radiation energy on the stimulable phosphor sheet 4 after read-out.

The stimulable phosphor sheet 4 is fed back and forth in the directions shown by arrows A and B by a pair of conveyer rollers 5 and a pair of light-shielding rollers 6 which are driven by an electric motor (not shown). The read-out section 2 comprises a laser 10 emitting a stimulating laser beam 11 and a galvanometer mirror 12 which is driven by an electric motor (not shown) and deflects the laser beam 11 to scan the upper surface of the stimulable phosphor sheet 4 in a main scanning direction. Art upper light guide 14a is disposed above the position in which the laser beam 11 impinges upon the stimulable phosphor sheet 11 and accumulates light emitted from the stimulable phosphor sheet 11 from above. A lower light guide 14b is disposed below the upper light guide 14a and accumulates light emitted from the stimulable phosphor sheet 11 from below. Further a light guide mirror 13 is disposed near the upper light guide 14a. The upper and lower light guides 14a and 14b are respectively connected to photomultipliers 15a and 15b which photoelectrically detect the light emitted from the stimulable phosphor sheet 11. The photomultipliers 15a and 15b are connected to a signal processing system 16. The light guides 14a and 14b are provided with cut-off filters (not shown) which prevent the laser beam 11 from entering the photomultipliers 15a and 15b.

The erasing section 3 comprises upper and lower erasing light sources 20a and 20b. The upper erasing light source 20a comprises three fluorescent tubes 21a arranged in a row along a sheet feed path along which the stimulable phosphor sheet 4 is fed and a fluorescent tube 21'a disposed on the end of the row remote from the read-out section 2. The lower erasing light source 20b comprises three fluorescent tubes 21b arranged in a row along the sheet feed path and a fluorescent tube 21'b disposed on the end of the row remote from the read-out section 2. The upper and lower erasing light sources 20a and 20b illuminate the stimulable phosphor sheet 4 passed through the light-shielding rollers 6 from above and below.

The three fluorescent tubes 21a of the upper erasing light source 20a and the three fluorescent tubes 21b of the lower erasing light source 20b are respectively covered with filters 22a and 22b for cutting light components of the erasing light emitted from the fluorescent tubes which components can be transmitted through the cut-off filter provided on the light guides 14a and 14b.

There have been known various types of fluorescent tubes. For example, cold cathode fluorescent tubes emitting green (G) light, blue (B) light, high color rendering white (LCD) light and the like can be employed as the erasing light sources 20a and 20b as well as normal fluorescent tubes emitting white (W) light, warm white (WW) light, daylight color (D) light, incandescent color light, high color rendering white (W-DL, W-SDL, W-EDL) light and the like. These fluorescent tubes have wide band spectra ranging from about 300 nm to 750 nm and wide and high emission distributions about 600 nm. Further the normal fluorescent tubes have bright line spectra about 450 nm and 550 nm.

As the filters 22a and 22b, a sharp cut filter which cuts light having a wavelength shorter than about 400 nm can be employed. For example, a sharp cut filter "L-42" (HOYA) which transmits only light having a wavelength not shorter than about 420 nm can be preferably used. Further "L-40" which transmits only light having a wavelength longer than about 390 nm to 410 nm can also be used.

The operation of the radiation image read-out and erasing apparatus 1 of this embodiment will be described, hereinbelow.

While a stimulable phosphor sheet 4, which has stored thereon a radiation image of an object, is conveyed in the direction of arrow A by the rollers 5 and 6 (sub scanning), the laser beam 11 from the laser 10 is deflected by the galvanometer mirror 12 to scan the upper surface of the stimulable phosphor sheet 4 in the direction substantially perpendicular to the direction of arrow A in which the stimulable phosphor sheet 4 is conveyed for the sub scanning. When the stimulable phosphor sheet 4 is exposed to the laser beam 11, the exposed portion of the stimulable phosphor sheet 4 emits light in an amount proportional to the amount of radiation energy stored thereon. The light emitted upward from the stimulable phosphor sheet 4 is guided by the upper light guide 14a and photoelectrically detected by the photomultiplier 15a. That is, the emitted light enters the light guide 14a through the light input face of the light guide 14a and is guided through repeated total reflection inside of the light guide 14a to be received by the photomultiplier 15a. In this manner, the amount of the emitted light representing the radiation image is converted into an electric signal by the photomultiplier 15a. Similarly the light emitted downward from the stimulable phosphor sheet 4 is guided by the lower light guide 14b and photoelectrically detected by the photomultiplier 15b.

The analog image signals respectively output from the photomultipliers 15a and 15b are input into the signal processing system 16 and logarithmically amplified and added together. Then the processed image signal thus obtained is input into a reproducing means to be reproduced as a visible image. The reproducing means may be, for instance, a display means such as a CRT or a recording means such as a light scanning recording system.

While the radiation image stored on the stimulable phosphor sheet 4 is read out, the fluorescent tubes 21a and 21b of the erasing light sources 20a and 20b are kept on with the fluorescent tubes 21'a and 21'b kept off and accordingly, the stimulable phosphor sheet 4 which is fed into the erasing section 3 after passing through the read-out section 2 is exposed to light emitted from the fluorescent tubes 21a and 21b through the filters 22a and 22b. The erasing light passing through the filters 22a and 22b is cut by the cut-off filters on the light guides 14a and 14b and cannot be detected by the photomultipliers 15a and 15b. Thus the erasing light passing through the filters 22a and 22b is prevented from generating noise in the reproduced radiation image.

When read-out of the radiation image on the whole stimulable phosphor sheet 4 is completed and the trailing end of the stimulable phosphor sheet 4 comes to be opposed to the fluorescent tubes 21'a and 21'b, the stimulable phosphor sheet 4 is stopped and reversed in the direction of arrow B. At this time, the fluorescent tubes 21'a and 21'b are turned on with the fluorescent tubes 21a and 21b of the erasing light sources 20a and 20b kept on. On the way to the read-out section 2, the stimulable phosphor sheet 4 is first exposed to light from the fluorescent tubes 21'a and 21'b without passing through any filter, whereby electrons trapped deep in the stimulable phosphor sheet 4 can be released. Since the fluorescent tubes 21'a and 21'b are sufficiently remote from the read-out section 2, the erasing light emitted therefrom and directly impinges upon the stimulable phosphor sheet 4 cannot be detected by the photomultipliers 15a and 15b. However it is preferred that the image read-out system is stopped when the stimulable phosphor sheet 4 is reversed to more surely prevent the erasing light from the fluorescent tubes 21'a and 21'b from being detected by the photomultipliers 15a and 15b. Thereafter the stimulable phosphor sheet 4 is again exposed to the erasing light which is emitted from the fluorescent tubes 21a and 21b and impinges upon the stimulable phosphor sheet 4 after passing through the filters 22a and 22b, whereby components excited by the erasing light from the fluorescent tubes 21'a and 21'b can be erased, if any, and the stimulable phosphor sheet 4 can be more cleanly erased.

Though, in the embodiment described above, fluorescent tubes are employed as the erasing light source, various fluorescent tubes, mercury vapor lamps, metal halide lamps, ultraviolet lamps and the like which emit light containing a wavelength component in the ultraviolet region may be employed as the erasing light source. In order to effect an efficient erasure, it is preferred that the erasing light contains visible light component in addition to the light component in the ultraviolet region. For this purpose, a high- or low-pressure sodium vapor lamp may be used in combination with an ultraviolet lamp. Also in this case, the erasing light should be projected onto the stimulable phosphor sheet through a filter not to be detected by the photomultiplier.

The mercury vapor lamp has several bright line spectra in the range from about 350 nm to 600 nm and can be employed as the erasing light source. Further a high-pressure sodium vapor lamp has a wide band spectra ranging from about 500 nm to 750 nm and contains relatively small amount of light component in the ultraviolet region. Accordingly, the high-pressure sodium vapor lamp should be employed in combination with an ultraviolet lamp. That is, the high-pressure sodium vapor lamp is used in the first erasure and the ultraviolet lamp is used in the second erasure.

Though having a bright line spectrum about 580 nm, the low-pressure sodium vapor lamp has no power available for the ultraviolet region. Accordingly, as the high-pressure sodium vapor lamp, the low-pressure sodium vapor lamp should be employed in combination with an ultraviolet lamp.

As such an ultraviolet lamp, there have been known a black light (BL) fluorescent tube, a fluorescent sunlamp, a BLE cold cathode fluorescent tube, a ULE cold cathode fluorescent tube and the like, any one of which has a very bright band spectrum between 300 nm and 400 nm.

Figure 2:
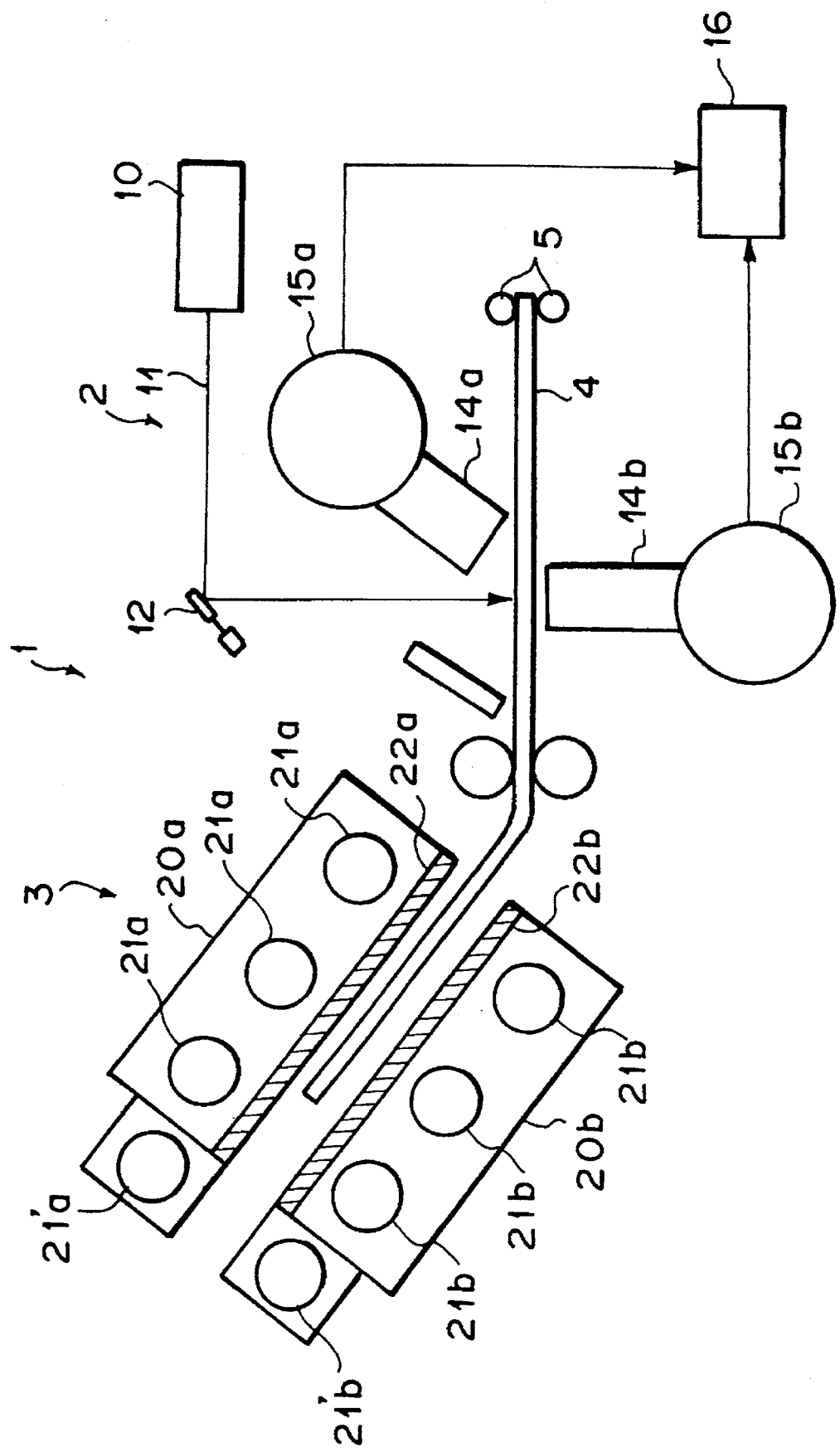
FIG. 2 is a schematic view of a radiation image read-out and erasing apparatus in accordance with another embodiment of the present invention.

Though, in the embodiment described above, the stimulable phosphor sheet 4 is horizontally held in the erasing section 3 as it is fed out from the read-out section 2, the erasing section 3 may be positioned at an angle relative to the read-out section 2 so that the stimulable phosphor sheet 4 is bent after fed out from the read-out section 2 and then fed into the erasing section 3 as shown in FIG. 2. With this arrangement, the erasing light becomes less apt to enter the read-out section 2.

Though, in the embodiments described above in conjunction with FIGS. 1 and 2, the stimulable phosphor sheet 4 is moved relative to the read-out section 2 and the erasing section 3 with the read-out section 2 and the erasing section 3 fixed during read-out and erasure, the read-out section 2 and the erasing section 3 may be moved with the stimulable phosphor sheet 4 fixed.

What is claimed is:

1. A radiation image read-out and erasing method for reading out a radiation image stored on a stimulable phosphor sheet and erasing the residual image information remaining on the stimulable phosphor sheet comprising the steps of reading out a radiation image stored on a stimulable phosphor sheet by exposing the stimulable phosphor sheet to stimulating rays, photoelectrically detecting light emitted by the stimulable phosphor sheet by a photoelectric read-out means and converting it into an electric image signal in a read-out section while feeding the stimulable phosphor sheet through a read-out section toward an erasing section, exposing the portion of the stimulable phosphor sheet which is fed to the erasing section after passing through the read-out section to first erasing light, and exposing the stimulable phosphor sheet to second erasing light while feeding the stimulable phosphor sheet through the erasing section toward the read-out section, wherein the improvement comprises that the first erasing light contains no light component in a wavelength range which can be detected by the photoelectric read-out means and the second erasing light contains a light component in the wavelength range which can be detected by the photoelectric read-out means.

2. A radiation image read-out and erasing method as defined in claim 1 in which after exposed to the second erasing light, the stimulable phosphor sheet is further exposed to third erasing light which contains no light component having a wavelength shorter than the light emitted from the stimulable phosphor sheet upon stimulation thereof.

3. A radiation image read-out and erasing method as defined in claim 1 or 2 in which the first erasing light has a wavelength longer than that of the light emitted from the stimulable phosphor sheet upon stimulation thereof, and the second erasing light contains a light component having a wavelength not longer than that of the light emitted from the stimulable phosphor sheet upon stimulation thereof.

4. A radiation image read-out and erasing apparatus for reading out a radiation image stored on a stimulable phosphor sheet and erasing the residual image information remaining on the stimulable phosphor sheet comprising a read-out section which has a stimulating ray source and a photoelectric read-out means, an erasing section which is disposed adjacent to the read-out section and is provided with first and second erasing light sources, and a sheet feeding means which moves the stimulable phosphor sheet relative to the read-out section and the erasing section through the read-out section to the erasing section and through the erasing section to the read-out section, the radiation image stored on the stimulable phosphor sheet being read out by exposing the stimulable phosphor sheet to stimulating rays from the stimulating light source, photoelectrically detecting light emitted by the stimulable phosphor sheet by the photoelectric read-out means and converting it into an electric image signal in said read-out section while the stimulable phosphor sheet is fed through the read-out section toward the erasing section by the sheet feeding means, and residual image information remaining on the stimulable phosphor sheet after read-out being erased by exposing the portion of the stimulable phosphor sheet which is fed to the erasing section after passing through the read-out section to first erasing light from the first erasing light source and exposing the stimulable phosphor sheet to second erasing light from the second erasing light source while the stimulable phosphor sheet is fed through the erasing section toward the read-out section, wherein the improvement comprises that the first erasing light contains no light component in a wavelength range which can be detected by the photoelectric read-out means and the second erasing light contains a light component in the wavelength range which can be detected by the photoelectric read-out means.

5. A radiation image read-out and erasing apparatus as defined in claim 4 in which the sheet feeding means operates such that the stimulable phosphor sheet is again exposed to the first erasing light from the first erasing light source which contains no light component having a wavelength shorter than the light emitted from the stimulable phosphor sheet upon stimulation thereof after being exposed to the second erasing light.

6. A radiation image read-out and erasing apparatus as defined in claim 4 or 5 in which the first erasing light has a wavelength longer than that of the light emitted from the stimulable phosphor sheet upon stimulation thereof, and the second erasing light contains a light component having a wavelength not longer than that of the light emitted from the stimulable phosphor sheet upon stimulation thereof.

* * * * *